(12) United States Patent
Makdissi et al.

(10) Patent No.: US 9,095,716 B2
(45) Date of Patent: Aug. 4, 2015

(54) AUTONOMOUS INTRACORPOREAL CAPSULE WITH DOUBLE ENERGY HARVESTING

(71) Applicant: SORIN CRM SAS, Clamart Cedex (FR)

(72) Inventors: Alaa Makdissi, Paris (FR); Martin Deterre, Paris (FR)

(73) Assignee: SORIN CRM SAS, Clamart Cedex (FR)

( * ) Notice: Subject to any disclaimer, the term of this patent is extended or adjusted under 35 U.S.C. 154(b) by 0 days.

(21) Appl. No.: 13/797,078

(22) Filed: Mar. 12, 2013

(65) Prior Publication Data
US 2013/0238073 A1    Sep. 12, 2013

(30) Foreign Application Priority Data
Mar. 12, 2012 (FR) ...................... 12 52216

(51) Int. Cl.
*A61N 1/378*    (2006.01)
*A61N 1/365*    (2006.01)

(52) U.S. Cl.
CPC .......... *A61N 1/36542* (2013.01); *A61N 1/3785* (2013.01)

(58) Field of Classification Search
CPC . A61N 1/378; A61N 1/3785; A61N 1/36542; A61N 1/36571; A61N 1/36578
USPC ........................................................ 607/126
See application file for complete search history.

(56) References Cited

U.S. PATENT DOCUMENTS

| | | | |
|---|---|---|---|
| 3,456,134 A | 7/1969 | Ko | |
| 3,943,936 A * | 3/1976 | Rasor et al. | ..................... 607/35 |
| 6,984,902 B1 | 1/2006 | Huang et al. | |
| 7,729,768 B2 | 6/2010 | White et al. | |
| 7,843,090 B2 | 11/2010 | Roberts et al. | |
| 2005/0256549 A1 | 11/2005 | Holzer | |
| 2006/0136004 A1 | 6/2006 | Cowan et al. | |
| 2007/0088397 A1 | 4/2007 | Jacobson | |
| 2007/0276444 A1 | 11/2007 | Gelbart et al. | |
| 2007/0293904 A1 | 12/2007 | Gelbart et al. | |
| 2009/0281600 A1 | 11/2009 | Lemieux | |
| 2010/0176664 A1 | 7/2010 | Roberts et al. | |
| 2010/0217354 A1 | 8/2010 | Weiss et al. | |
| 2010/0217364 A1 | 8/2010 | Hadas | |

FOREIGN PATENT DOCUMENTS

| | | |
|---|---|---|
| DE | 10 2004 043 002 | 3/2006 |
| WO | WO-2007/047681 A2 | 4/2007 |

OTHER PUBLICATIONS

Preliminary Search Report for French Patent Application No. 1252216, dated Jun. 8, 2012, 2 pages.

\* cited by examiner

*Primary Examiner* — Joseph Dietrich
(74) *Attorney, Agent, or Firm* — Foley & Lardner LLP (57) ABSTRACT

A intracorporeal medical capsule is shown and described. The capsule includes an elastically deformable base having an anchor at one end and coupled to a capsule body at the opposite end. An energy harvesting element is elastically coupled to a seismic mass within the capsule body. The elastically deformable base increases energy harvested at the energy harvesting element due to elastic movement of the capsule body in the presence of blood flow around the capsule body.

20 Claims, 4 Drawing Sheets

AUTONOMOUS INTRACORPOREAL CAPSULE WITH DOUBLE ENERGY HARVESTING

CROSS-REFERENCE TO RELATED PATENT APPLICATIONS

The present application claims the benefit of and priority to France Priority Application 1252216, filed Mar. 12, 2012, under 35 U.S.C. §119. The entirety of France Priority Application 1252216 is incorporated herein by reference.

BACKGROUND

The present invention relates to the field of "medical devices" as may be defined, for example, by the Jun. 14, 1993 directive 93/42/CE of the European Communities. The present invention may also relate to the "active implantable medical devices" field as defined, for example, by the Jun. 20, 1990 directive 90/385/CEE of the European Communities.

Such devices may include implantable medical devices that continuously monitor a patient's cardiac rhythm and deliver electrical pulses to the heart for cardiac stimulation, resynchronization, cardioversion, and/or defibrillation in case of a rhythm disorder detected by the device. Such devices also include neurological devices, cochlear implants, etc., as well as devices for pH measurement or devices for intracorporeal impedance measurement (such as the measure of the transpulmonary impedance or of the intracardiac impedance). The invention particularly relates to autonomous implanted capsules and are free from any physical connection to a main implanted device (for example, the can of a stimulation pulse generator).

Recent advances in microfabrication and biotechnology have allowed the development of a wide variety of such miniaturized implantable devices, providing physicians with less invasive implantation procedures, providing more comfort for patients, providing increased performance, and providing access to new types of diagnostics and treatments.

The invention also relates to autonomous capsules implanted without any physical connection to a main device (e.g., a stimulation pulse generator). These autonomous capsules may be called "leadless capsules" to distinguish them from the electrodes or sensors placed at the distal end of a lead.

Implants without lead or leadless capsules are for example described in U.S. 2007/0088397 A1 and WO 2007/047681 A2 (Nanostim, Inc.) or in the U.S. 2006/0136004 A1 (EBR Systems, Inc.).

The leadless capsules can be e.g. epicardial capsules fixed to the outer wall of the heart, or endocardial capsules, fixed to the inner wall of a ventricular or atrial cavity through a projecting anchoring screw axially extending the capsule body and for penetrating into the cardiac tissue by screwing at the implant site. The invention is more specifically dedicated to endocardial capsules.

A leadless capsule includes sensing/pacing circuits to collect myocardium depolarization potentials and/or to apply stimulation pulses to the site where the capsule is implanted. The latter includes then an appropriate electrode which can be formed by an active portion of the anchoring screw. It can also, alternatively or in addition, incorporate, one or more sensors to locally measure the value of a parameter such as the level of oxygen in the blood, the heart intracardiac pressure, the acceleration of the heart wall, the acceleration of the patient as an indicator of activity, etc.

The leadless capsules also incorporate transmitter/receiver wireless communication means to remotely exchange data.

Whatever the implemented technique, the signal processing within the capsule and its remote transmission requires significant energy compared to energy resources that can store the capsule. However, due to its autonomous nature, the capsule can only use its own resources such as an energy harvesting circuit associated with a small integrated buffer battery.

Energy harvesting systems for leadless capsules have been proposed. However, such systems rarely provide enough power to supply a regular capsule. Moreover, keeping a capsule with an energy harvester small is a challenge.

Following the examples of U.S. Pat. Nos. 6,984,902 and 7,843,090, the majority of energy harvesting systems today are based on an inertial device, that is to say, using the acceleration of the environment to act on a mass, known as "seismic mass", whose relative movement with respect to a piezoelectric electromagnetic or electrostatic transducer, generates an electrical magnitude.

The U.S. Pat. Nos. 7,729,768, 3,456,134 and U.S. 2010/0217364 proposes a configuration in which an inertial harvester in which an oscillating seismic mass and associated energy harvesting methods are disposed in a chamber, within a housing of a leadless capsule. This mass can be driven in at least one degree of freedom by the overall movement of the capsule, which allows harvesting methods to convert movement of the seismic mass relative to the housing into electrical energy. The amount of converted energy is proportional to the mass and thus the volume of the seismic mass, and is directly related to the amplitude of the vibration acceleration to which the mass is subjected. The capsule is in direct contact with the heart tissue via a rigid base.

The U.S. 2007/0293904 A1 discloses a further energy harvesting device, wherein the variations of blood pressure deform a bellows-shaped housing anchored to the cardiac wall, with resonance of an oscillating mass controlling a piezoelectric or electromagnetic generator.

An object of the invention is to provide a leadless capsule that would simultaneously harvest energy from seismic mass movements of the walls of organs and from the forces (e.g., turbulences) of fluid flows (e.g., blood flow) while retaining a small size.

Some embodiments achieve this object with an autonomous intracorporeal medical capsule including a housing defining a chamber in which an oscillating seismic mass and harvesting methods to convert a relative movement of the seismic mass relative to the housing into electrical energy. The capsule further includes methods for anchoring the housing to a wall of an organ of a patient. The capsule further may include an elastically deformable base connected to the housing at a first end and carrying the anchoring at a second end.

From a dynamic point of view, the seismic mass of the capsule according to the invention is subject to the forces provided by movements of the organ wall that are transmitted by the base. According to the invention, the seismic mass is further subject to fluid forces on the capsule, due to the fact that the elasticity of the base allows the housing to move relative to the wall. In the prior art, this fluid component is not present because the base is rigid and is intended to severely restrict the movement of the housing.

It is therefore possible to harvest both the mechanical energy of the movements of the walls of organs and that provided by the fluid flow, without the need to increase the weight or volume of the seismic mass.

Another advantage of the invention relates to the anchoring of the capsule. In the prior art, the capsule is rigidly attached to the wall, resulting in the forces and turbulence of blood flow exerted on the capsule being mechanically transmitted to the anchoring point in the cardiac wall. These forces end to weaken the system, with the risk of tearing the capsule. With the invention, this risk is reduced by the elasticity of the base, which is advantageously able to absorb applied fluid forces without transmitting them to the tissue anchor.

As discussed in more detail below, the inertial system formed by the capsule according to the invention can be modeled by two coupled oscillators, one formed by the seismic mass oscillating in the housing, and the other by the housing itself oscillating relative to the organ wall at the end of the elastically deformable base.

The spectrum of the relative displacement of the seismic mass has a wider frequency band resulting in a more effective energy harvesting. According to some embodiments of the invention, the mass and the coefficients of restoring forces of the seismic mass and of the housing are selected such that the displacement of the seismic mass relative to the capsule housing has a first maximum between 0.5 and 10 Hz and a second maximum between 12 and 40 Hz. This advantageous arrangement has the effect of aligning the frequency of the maxima of the spectrum of the relative displacement of the seismic mass with typical frequency intervals of blood flow pulses (0.5 to 10 Hz) and of motion of the heart walls (15 to 40 Hz).

In a particular exemplary embodiment, the first maximum is 1.2 Hz and the second maximum is located at 18 Hz.

According to a first embodiment, the seismic mass and the base are configured so that the oscillating movement of the seismic mass and the deformation movement of the base are made in longitudinal main directions, oriented perpendicularly to the wall of the organ of the patient. According to a second embodiment, the seismic mass and the base are configured so that the oscillating movement of the seismic mass and the deformation movement of the base are made in transverse main directions, oriented parallel to the wall of the organ of the patient.

One or both oscillating elements may be or include a spring such as a spiral spring, a helical spring, or an elastic girder.

The capsule according to the invention may include provisions for reversible attachment of the housing on the base. In such embodiments, it may be advantageously easy to replace the capsule without removing the anchor from the cardiac tissue.

An autonomous intracorporeal capsule is shown and described. A housing defines a chamber in which an oscillating seismic mass and an energy harvesting device are arranged. The energy harvesting device converts relative movement of the seismic mass to energy. The capsule also includes an anchoring device for coupling the housing to the wall of an organ of a patient. The capsule further includes an elastically deformable base connected to the housing at a first end and carrying the anchoring at a second end.

One embodiment relates to an intracorporeal medical capsule. The capsule includes a housing defining a chamber. The chamber houses an oscillating seismic mass and an energy harvester that converts movement of the seismic mass relative to the energy harvester into electrical energy. The capsule further includes an anchor for anchoring the housing to a wall of an organ of a patient. The capsule also includes an elastically deformable base between the housing at a first end and the anchor at a second end. The masses ($m_1$, $m_2$) and the elastic coefficients ($k_1$, $k_2$) of the seismic mass and of the housing may be such that the spectrum of the relative movement (U) of the seismic mass relative to the housing has a first maximum between 0.5 and 10 Hz and a second maximum between 15 and 40 Hz. The first maximum may be 1.2 Hz.

The second maximum may be 18 Hz. The coefficients ($k_1$, $k_2$) of the restoring forces of the oscillating seismic mass and of the housing may have a ratio equal to 1. The seismic mass and the base may be located so that the oscillating movement of the seismic mass and the deformation movement of the base are coaxial and are perpendicular to the wall of the patient's organ. The seismic mass and the base may be located so that the oscillating movement of the seismic mass and the deformation movement of the base may be transverse main directions oriented parallel to the wall of the patient's organ. The elastically deformable element provides for oscillation of the seismic mass. The elastically deformable element may be or include at least one of: a cantilever beam, an engraved spring, and a spiral spring. The elastically deformable base may be or include at least one of: a coil spring and a cantilever beam. The capsule further includes methods for reversible attachment of the housing on the base.

Another embodiment relates to an intracorporeal medical capsule. The capsule includes an elastically deformable base having an anchor at one end and coupled to a capsule body at the opposite end. The capsule further includes an energy harvesting element elastically coupled to a seismic mass within the capsule body. The elastically deformable base increases energy harvested at the energy harvesting element due to elastic movement of the capsule body in the presence of blood flow around the capsule body.

Another embodiment relates to a method for harvesting energy in an intracorporeal medical capsule for a heart. The method includes anchoring an elastically deformable base to a wall of tissue within the heart. The method further includes receiving mechanical energy via movement of the wall, a seismic mass elastically coupled inside the capsule to an energy harvesting element. The method further includes receiving mechanical energy via movement of blood in the heart using the elastically deformable base. The method also includes utilizing, by the energy harvesting element, the mechanical energy received via the movement of the wall and the mechanical energy received via the movement of blood in the heart.

DETAILED DESCRIPTION

With reference to the drawing FIGS. 1 to 10c, various embodiments of the invention are described.

Figure 1:
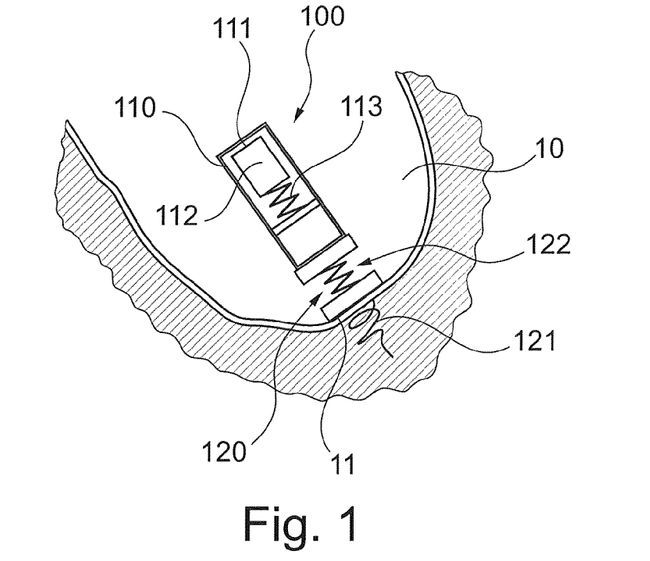
FIG. 1 is a side view of a capsule placed in a heart chamber, according to an exemplary embodiment.

In FIG. 1, an intracorporeal autonomous leadless type capsule 100 is shown. The capsule 100 includes a housing 110 and a base 120. The base 120 includes an anchor 121 for securing the capsule to a wall 11 of a heart chamber 10 of a patient. In the example of FIG. 1, the anchor 121 is a screw.

For the sake of clarity, the capsule 100 includes many elements that are not shown in FIG. 1, such as an electrode (which can be incorporated in the anchoring screw 121) to transmit myocardium depolarization potentials or to apply stimulation pulses to the heart wall 11. Sensors may be incorporated into the capsule 100, such as blood oxygen level sensors, cardiac pressure sensors or other sensors, as well as wireless communications electronics (e.g., transmitters, receivers, etc.).

In an exemplary embodiment, energetic autonomy of the capsule 100 is provided by a energy harvesting system. The energy harvesting system may use an inertial device which takes advantage of the acceleration experienced by the environment in which the capsule is mounted, to move a seismic mass 112 oscillating under the action of a spring 113 within a chamber 111 of the housing 110. The movement of the seismic mass relative to the housing is converted into electrical energy by an energy harvester disposed in the chamber 111. The energy harvester may be or include a piezoelectric transducer, an electromagnetic generator, or an electrostatic transducer.

The base 120 may be made of an elastically deformable body 122 connected to the housing 110 at a first end and bearing the anchor 121 at a second end. In FIG. 1, the elastically deformable body is shown as spring 122.

The embodiment of FIG. 1 advantageously harvests both: (i) the movements of the heart wall and (ii) fluidic forces within the cavity 10. In conventional systems, harvesting applies only to the movements of the wall, the base being rigid and not elastically deformable.

Figure 2:
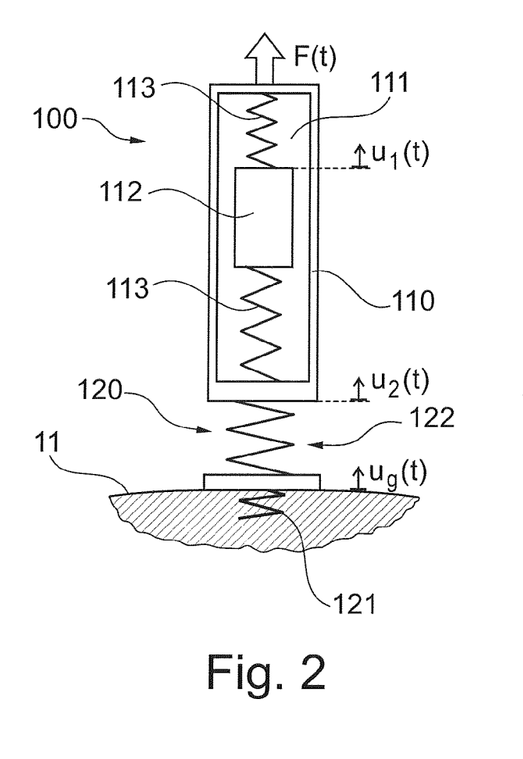
FIG. 2 is a schematic side view of the capsule of FIG. 1, according to an exemplary embodiment.

FIG. 2 is a diagram of the capsule 100 in a longitudinal fluidic excitation mode, in that the seismic mass 112 and the base 120 are configured such that the oscillating movement of the seismic mass and the deformation movement of the base are made longitudinally in a direction substantially normal to the wall 11 corresponding to the axis of the capsule 100.

Figure 3:
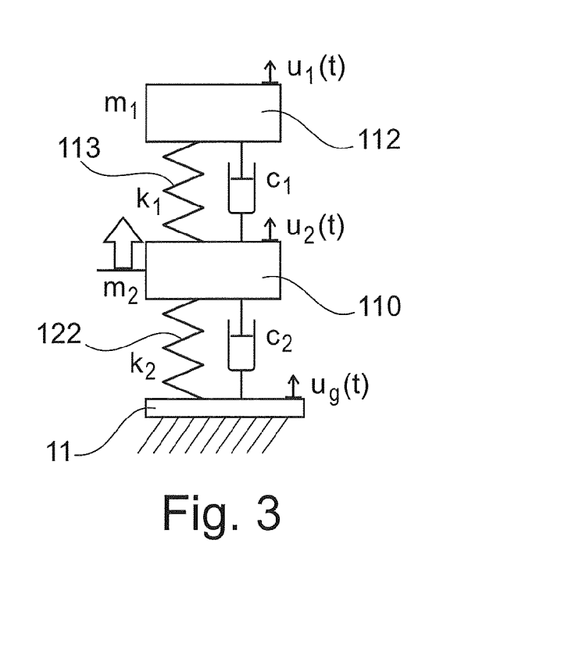
FIG. 3 is an equivalent dynamic diagram of the capsule of FIGS. 1 and 2, according to an exemplary embodiment.

FIG. 3 is a dynamic model of the capsule of FIG. 2: $m_1$ is the seismic mass 112, $k_1$ is the stiffness of the spring 113, $c_1$ the viscous friction constant, $m_2$ is the mass of the housing 110 and of the fixed parts associated with the capsule (electronics, sensors, etc.), $k_2$ is the stiffness of the spring 122 equivalent to the base 120 and $c_2$ the mechanical losses thereof.

Moreover, $u_g$, $u_1$ and $u_2$ are the respective displacements of the heart wall 11, of the housing 110 and of the seismic mass 112. Finally, F is the longitudinal excitation force due to forces developed by the surrounding fluid on the capsule 100.

Note that the coefficient $c_1$ represents both the transduction coupling and the mechanical losses in viscous form. The latter are very small compared to the amortization of transduction and can be neglected. For the same reason, the coefficient $c_2$ can be neglected compared to $c_1$.

The fundamental equation of dynamics applied to the system of FIG. 3 can be written in matrix form as follows:

$$\begin{pmatrix} m_1 & 0 \\ 0 & m_2 \end{pmatrix}\begin{pmatrix} \ddot{u}_1 \\ \ddot{u}_2 \end{pmatrix} + \begin{pmatrix} c_1 & -c_1 \\ -c_1 & c_1+c_2 \end{pmatrix}\begin{pmatrix} \dot{u}_1 \\ \dot{u}_2 \end{pmatrix} + \begin{pmatrix} k_1 & -k_1 \\ -k_1 & k_1+k_2 \end{pmatrix}\begin{pmatrix} u_1 \\ u_2 \end{pmatrix} = \begin{pmatrix} 0 \\ k_2 u_g + c_2 \dot{u}_g + F \end{pmatrix} = P$$

where this equation is decoupled by linearity into two components P1, P2:

$$P = \begin{pmatrix} 0 \\ P_1 + P_2 \end{pmatrix}$$

and where $P_1 = k_2 u_g + c_2 \dot{u}_g$ represents the forces due to seismic movements of the wall, and F corresponds to the fluid forces applied on the capsule 100 into the cavity 10. Assuming the load Pi(i=1, 2) is harmonic at the angular frequency ω and passing in complex representation, the amplitude U=U1−U2 of the relative position of the seismic mass 112 is given (neglecting $c_2$ to $c_1$) by:

$$U = \frac{P_i \omega_c^2 / k}{\alpha + 2i\alpha\xi\omega_c - (1+\alpha+\beta)\omega_c^2 - 2i(1+\beta)\xi\omega_c^3 + \beta\omega_c^4}$$

In this expression of U, the following notation changes were made:

$k_1 = k$, $k_2 = \alpha k_1 = \alpha k$, $m_1 = m$, $m2 = _{\beta m 1} = \beta m$, $c_1 = c$, $\omega n = \sqrt{k/m}$, $\omega c = \omega / \omega n$, $\xi = c_1 / (2\sqrt{km})$ The normalized pulse $\omega_c$ is thus the angular frequency ω of the forces applied reduced to the angular frequency ω, of the oscillating seismic mass 112. We can deduce from the above formula the expression of U for each source of energy, namely:

For cardiac movements: $P_1 = k_2 u_g = \alpha k u_g$, where:

$$U = \frac{\alpha \omega_c^2}{\alpha + 2i\alpha\xi\omega_c - (1+\alpha+\beta)\omega_c^2 - 2i(1+\beta)\xi\omega_c^3 + \beta\omega_c^4} u_g$$

For fluid forces: $F = P2$, where:

$$U = \frac{\omega_c^2}{\alpha + 2i\alpha\xi\omega_c - (1+\alpha+\beta)\omega_c^2 - 2i(1+\beta)\xi\omega_c^3 + \beta\omega_c^4} \frac{F}{k}$$

Figure 4:
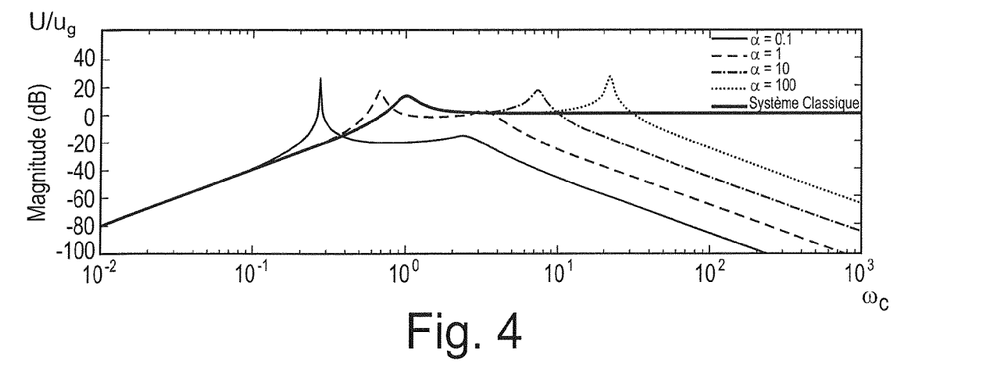
FIG. 4 shows a Bode diagram of the ratio in dB of the displacement U of the seismic mass of FIG. 3 and of the displacement $U_g$ of the heart wall according to the normalized pulse $\omega_c$, for different values of the parameter $\alpha$.
Figure 5:
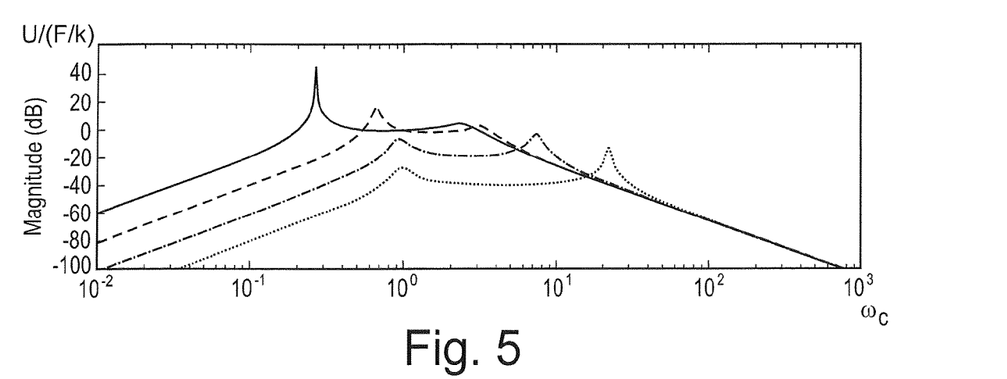
FIG. 5 shows a Bode diagram of the ratio in dB of the displacement U of the seismic mass of FIG. 3 and of the displacement due to fluid F/k as a function of the normalized pulse $\omega_c$, for different values of the parameter $\alpha$.

FIGS. 4 and 5 are Bode diagrams showing how respectively $U/U_g$ and $U/(F/k)$ vary (in dB), based on the normalized frequency $\omega_c$, for different values of the parameter $\alpha=k_2/k_1$. Applicants submit that these diagrams illustrate a wideband frequency in which the harvesting is performed with much greater efficiency than that of the inertial devices of the prior art. Furthermore, embodiments of the invention can provide two maxima, or peaks, exist for which harvesting is optimal. These peaks correspond to resonances at pseudo-frequencies of the mechanical seismic mass/housing with two degrees of freedom of oscillation.

The behavior of these curves as a function of the parameter $\alpha$ can be interpreted as follows. Regarding the horizontal behavior, we find that when $\alpha$ is small, the two peaks shift to the left for the two curves. The system is generally more flexible. When $\alpha$ is large, the first peak tends to $\omega_c=1$, the second peak moves away for the two curves. In the limiting case where $\alpha=\infty$, there is a single peak at $\omega_c=1$. We are then in the classic situation of the prior art wherein $k_2=\infty$ and for which only the heart wall motions are harvested at the resonance frequency $\omega n$ of the seismic mass.

Regarding the horizontal behavior, we can see that when a decreases, the plateau level of the $U/u_g$ curve falls while that of $U/(F/k)$ tends to 1. More fluid forces that wall motion forces are then harvested. When $\alpha$ increases, the opposite is true: the plateau level of the $U/u_g$ curve tends to 1 while that of $U/(F/k)$ decreases. In conclusion, if one wants to equally harvest the wall movements and the fluidic efforts, $\alpha=1$ may provide good performance.

Figure 6:
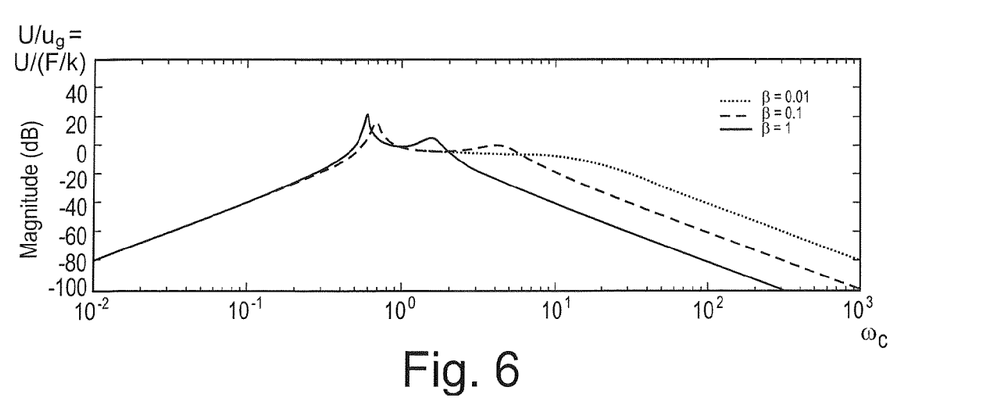
FIG. 6 is a Bode diagram of the ratio in dB of the displacement U of the seismic mass of FIG. 3 and of the displacement $U_g$ of the heart wall or of the displacement due to fluid F/k as a function of the normalized pulse $\omega_c$, for different values the parameter $\beta$ and for $\alpha=1$.

FIG. 6 is a Bode diagram for $\alpha=1$ giving changes in dB of $U/u_g = U/(F/k)$ as a function of the normalized frequency $\omega_c$, for different values of the parameter $\beta=m_2/m_1$.

In general, if $\beta$ increases, the peaks come closer, shift to the left and amplify. It is therefore preferable to increase $\beta$ for greater resonance peaks while trying to match the peaks with the excitation spectra located between 0.5 and 10 Hz for blood flows, and between 15 and 40 Hz for the cardiac movements, the preferred frequencies being respectively of 1.2 Hz and 18 Hz. It might be assumed that the heart wall varies with an amplitude $u_g$ of a few millimeters during heartbeat.

The force F of the fluid can also be modeled, especially in the case of a force perpendicular to the device, by the drag applied by the blood flow. In this case, the magnitude of this force can be quantified as periodically varying according to the cardiac cycle by the formula:

$$F = \tfrac{1}{2} C \rho S V^2$$

wherein C is the drag coefficient (which is about 0.5 for a cylinder as the device shown in the figures), $\rho$ is the density of blood (about 1000 kg/m3), S is the effective area next to the fluid (of the order of 50 mm$^2$) and V is the speed of blood (about 1 m/s for the top of the variation range). Thus, in this example, a force F has a magnitude of ten mN.

The mass $m_2$ is due to the housing and to the electronics, a volume of about 150 mm$^3$, which is divided into 100 mm$^3$ for the electronics and 50 mm$^3$ for the case, which is a few tenths of grams. The seismic mass $m_1$, which must be designed to be large and therefore in a very dense material such as tungsten, weighs from one to a few grams. Thus, the value of $\beta=m_2/m_1$ is about a few tenths, typically 0.2.

The value of $\alpha$, determined by the shape and nature of the stiffness $k_2$ can be adjusted, in particular around 1, during the design of the harvester. The value of $\xi$, the damping is selected to about 0.1, which is the order of magnitude generally giving the best compromise bandwidth/power/displacement.

Figures 7A, 7B:
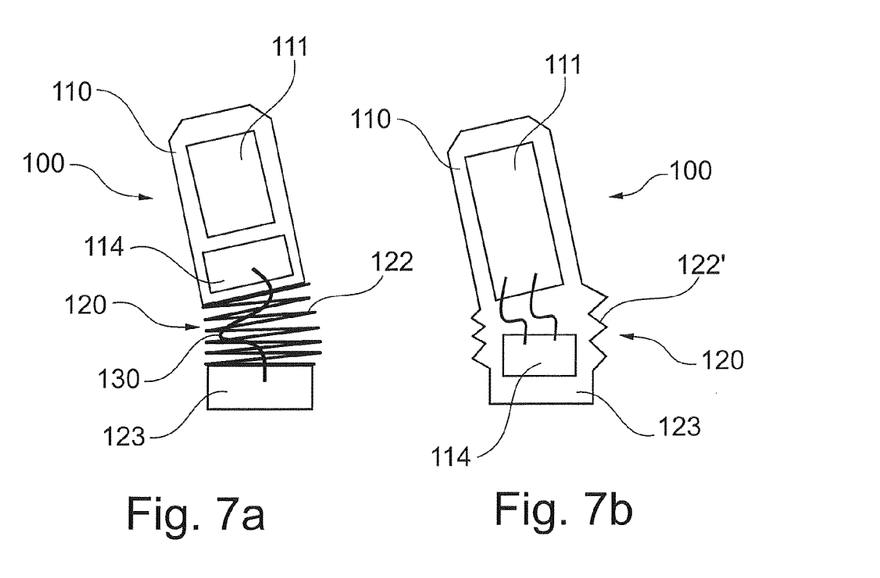
FIG. 7a is a side view of a first embodiment of a capsule according to one embodiment of the invention.
FIG. 7b is a side view of a second embodiment of a capsule according to another embodiment of the invention.

FIG. 7a illustrates a first embodiment of the capsule 100. An electronics module 114 is positioned in the housing 110. The fixed flange 123 located at one end of the base 120 allows the anchoring of the capsule 100 in the heart tissue by the above-described screw (anchoring the base's fixed flange 123 to the tissue).

The flexible member 122 provides the mechanical coupling between the housing of the capsule and the heart wall movement sustained by the base 120. This flexible element may be or include a metal spring. In this embodiment only the mobile housing 110 is sealed. A flexible conductor 130 may be used to interface the electronic module 114 with one or more electrodes located in the flange 123.

According to the second embodiment shown in FIG. 7b, the electronic module 114 and the chamber 111 for energy harvesting are positioned in an articulated tube. A flexible joint can be achieved for example by a bellows 122' (i.e., hollow flexible membrane or tube). Sealing can be provided at the interface between the tube and the electrodes at the end of the flange 123.

The housing 110 and the base 120 can be detached by a reversible fixation device in order to improve the modularity of the capsule.

Figure 8A:
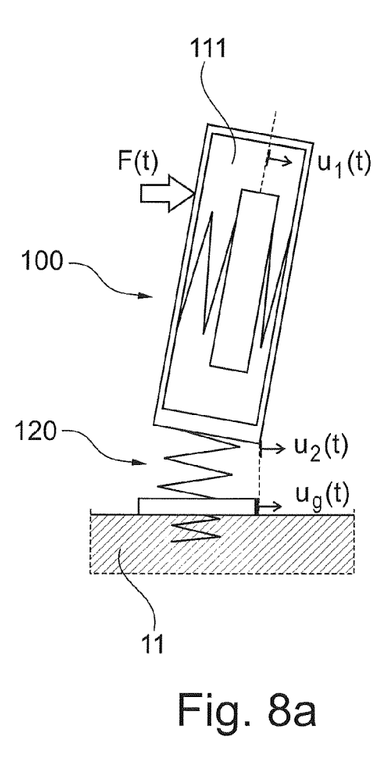
FIG. 8a is a schematic side view of a first embodiment of a capsule configured for lateral excitation.
Figure 8B:
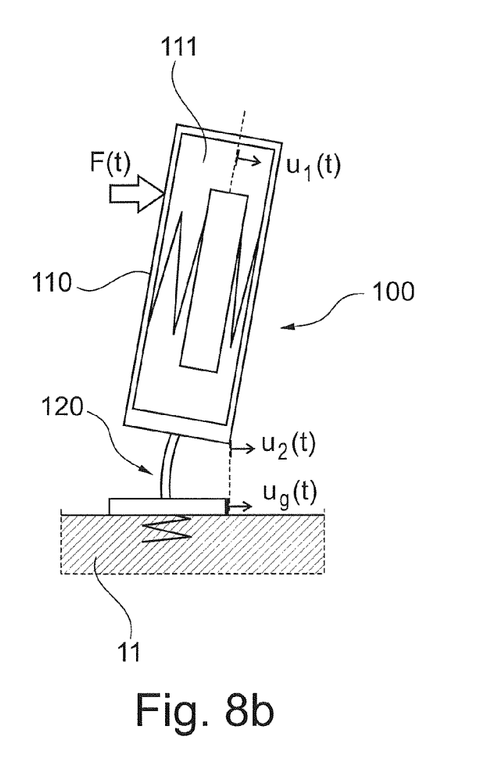
FIG. 8b is a schematic side view of a second embodiment of a capsule configured for lateral excitation.

Concerning the implementation and design of the internal spring 113 of the oscillating mass 112 and of the outer spring 122 of the base 120, it may be helpful to distinguish between two main modes of operation, namely the longitudinal mode shown in FIG. 2 and the lateral mode shown in FIGS. 8a and 8b. The mode may depend on the excitation direction: perpendicular or parallel to the cardiac wall 11.

In one embodiment, $\alpha=1$ (as an example of advantageous compromise shown in the Bode diagrams above) and wherein it is expected for $\omega_c$ to equal to about 0.5 (corresponding to the most important peak of the curves). In the case of excitation at about $\omega=20$ Hz (that is to say, a strong component of a typical heartbeat), then: $\omega_n=\omega/\omega_c=2\cdot 2\pi\cdot 20 \approx 250$ rad/s, a stiffness $k \approx 250$ N/m with $m_1 \approx 4$ g.

For the oscillating device, the seismic mass 112 of about 4 g may be advantageously obtained by using a very dense material such as tungsten, with for example dimensions of about 8×5×5 mm$^3$.

Figure 9A:
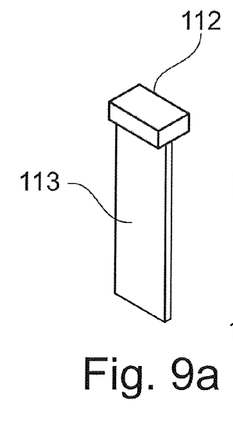
FIG. 9a is a perspective view of a first embodiment of the oscillation means of the seismic mass.

One method for obtaining the internal spring 113 is to provide a single beam as that shown in FIG. 9a, especially if lateral forces are to be harvested in accordance with FIGS. 8a and 8b. To achieve a stiffness coefficient $k_1=k=250$ N/m, this beam can have the following geometric properties: Young's modulus=150 GPa (order of magnitude for many metals), width=5 mm, thickness=75 μm, length=7.5 mm. The stiffness may be determined by the formula after the theory of Euler-Bernoulli for a free cantilever-beam: $k=E\cdot w\cdot(t/L)^{3/4}$, wherein E is the Young's modulus of the material, t is the thickness of the beam, w its width and L its length.

Figure 9B:
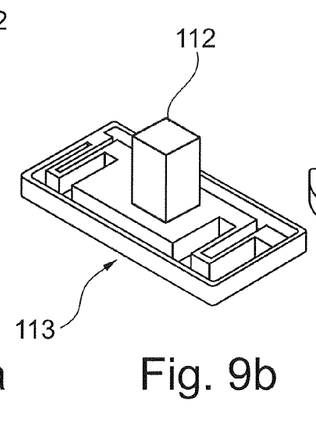
FIG. 9b is a perspective view of a second embodiment of the oscillation means of the seismic mass.

In another embodiment, the internal spring may also be microstructured in silicon by deep etching of a plate, according to the device of FIG. 9b. To obtain the desired stiffness, another formula, according to the beam theory for such springs, may be used: $k=2\cdot E w\cdot(t/L)^{3/n}$ wherein E is the Young's modulus of the material (about 150 GPa silicon), w is the thickness of the springs, t their width, L the length of each arm of the springs and n the number of arms constituting of each spring, that is n=2 in the case of FIG. 9b. For $k_1=250$ N/m, springs of 500 μm in height, 75 μm in thickness and 5 mm in length can be structured in a conventional silicon wafer. Depending on the orientation which is given to the device, this spring can be used in lateral or longitudinal configuration, provided that the mass adhering to the spring has a form compatible with the overall conditioning.

Figure 9C:
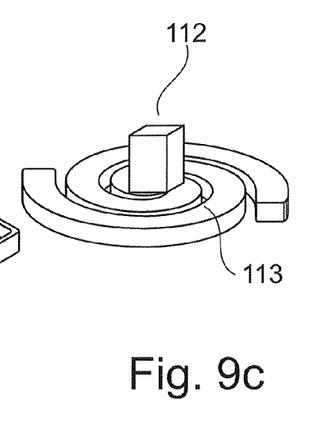
FIG. 9c is a perspective view of a third embodiment of the oscillation means of the seismic mass.

In yet another embodiment, an internal spring for seismic mass is designed in a spiral shape, as shown in FIG. 9c. This case is particularly suitable for longitudinal energy harvesting. Properties of this spiral can include, for example: diameter=4 mm, two arms making each one revolution, having a length of about 10 mm, a width of 500 μm and a thickness of 250 μm. For the outer spring, in the case previously detailed wherein α=1, the stiffness $k_2$ must also be about 250 N/m.

Figures 10A, 10B:
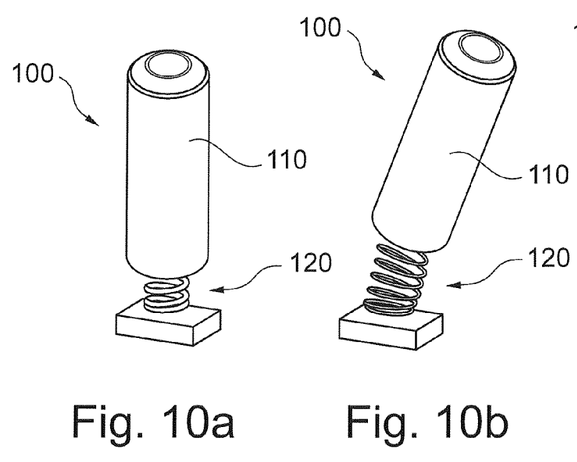
FIG. 10a is a perspective view of a first embodiment of a mechanism for elastic deformation of the base.
FIG. 10b is a perspective view of a second embodiment of a mechanism for elastic deformation of the base.

In an example suited particularly well for longitudinal excitation, one can for example take a helical spring as shown in FIG. 10a. The stiffness of this spring is given by: $k=E·d^4/(16·(1+v)(D-d)^3·n)$, depending on the diameter d of the wire, of the diameter D of the spring, of the Young's modulus E, of the Poisson's ratio v and of the number of turns n. The spring can thus be made of metal, for example titanium, having an outer diameter of 3 mm and a wire diameter of 250 μm, and having n=5 turns.

Figure 10C:
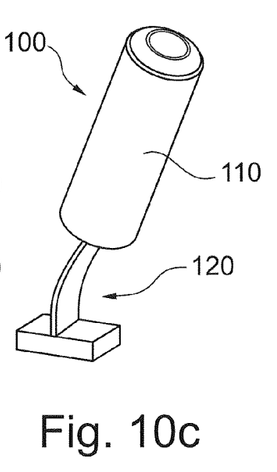
FIG. 10c is a perspective view of a third embodiment of a mechanism for elastic deformation of the base.

In an example suited particularly well for lateral excitation, one can use a single coil spring, but biased in flexion, as shown in FIG. 10b. A numerical simulation has shown that a stiffness of 250 N/m could be obtained with a design, similar to the preceding dimensioning, wherein the spring has an outer diameter of 3 mm, a number of turns equal to 5 and a diameter of wire of 375 μm. A beam spring of the type shown in FIG. 10c, similar to the version of the internal spring in FIG. 9a, may also be used, in lateral excitation. The beam may be made of a flexible material such as a polymer. For example, it may be made of PEEK (PolyEther Ether Ketone), having a length of 4 mm, a thickness of 200 μm and a width of 3 mm.

It should be noted that the various spring elements described herein can be combined to harvest mechanical energy or movement in several directions at once.

Once a variable relative displacement U is obtained between the seismic mass 112 and the housing 110, one or more energy harvesters can be used, for example:

Electromagnetic—such as those described in U.S. 2010/0176664: a device creates a magnetic field, for example with a permanent magnet (which may also be the seismic mass), while another element includes a circuit in relative motion relative to the first circuit and an induction current is caused.

Electrostatic—a set of electrodes facing each other, thereby creating a capacitor. During a relative movement, the capacity of the capacitor varies, either by changing the air gap, or by changing the facing surfaces. This change in capacitance can be converted into energy externally or through electret preloading of the capacitor when its capacity is high and discharging it when its capacity is low.

Piezoelectric—the spring is formed at least partially of a piezoelectric material and arranged between two mechanical objects under force, and is thereby subject to deformation in a relative movement. When deformed, electrical charges are created directly piezoelectricity on electrodes placed at the ends of the piezoelectric element.

What is claimed is:

1. An intracorporeal medical capsule, comprising:
a housing defining a chamber, wherein the chamber houses an oscillating seismic mass and an energy harvester that converts movement of the seismic mass relative to the energy harvester into electrical energy;
an anchor for anchoring the housing to a wall of an organ of a patient; and
an elastically deformable element having a first end extending from an exterior surface of the housing and a second end coupled to a base comprising the anchor;
wherein movement of the seismic mass is caused both by movement of the housing induced by movement of the wall of the organ of the patient to which the housing is anchored, and by movement of housing relative to the wall of the organ by way of the elastically deformable element and caused by the presence of blood flow around the capsule body.

2. The capsule of claim 1, wherein the masses ($m_1$, $m_2$) and the elastic coefficients ($k_1$, $k_2$) of the seismic mass and of the housing are such that the spectrum of the relative movement (U) of the seismic mass relative to the housing has a first maximum between 0.5 and 10 Hz and a second maximum between 15 and 40 Hz.

3. The capsule of claim 2, wherein the first maximum is at 1.2 Hz.

4. The capsule of claim 2, wherein the second maximum is at 18 Hz.

5. The capsule of claim 1, wherein the coefficients ($k_1$, $k_2$) of the restoring forces of the oscillating seismic mass and of the housing are in a ratio equal to 1.

6. The capsule of claim 1, wherein the seismic mass and the elastically deformable element are located so that the oscillating movement of the seismic mass and the deformation movement of the elastically deformable element are coaxial and are perpendicular to the wall of the patient's organ.

7. The capsule of claim 1, wherein the seismic mass and the elastically deformable element are located so that the oscillating movement of the seismic mass and the deformation movement of the elastically deformable element are transverse main directions oriented parallel to the wall of the patient's organ.

8. The capsule of claim 1, comprising a second elastically deformable element providing for oscillation of the seismic mass, wherein the second elastically deformable element comprises at least one of: a cantilever beam, an engraved spring, and a spiral spring.

9. The capsule of claim 1, wherein the elastically deformable element comprises at least one of: a coil spring and a cantilever beam.

10. The capsule of claim 1, comprising means for reversible attachment of the housing on the base.

11. An intracorporeal medical capsule, comprising:
an elastically deformable element having an anchor at one end and coupled to an exterior surface of a capsule body at the opposite end; and
an energy harvesting element elastically coupled to a seismic mass within the capsule body;
wherein the elastically deformable element increases energy harvested at the energy harvesting element due to elastic movement of the capsule body in the presence of blood flow around the capsule body.

12. The capsule of claim 11, wherein the masses ($m_1$, $m_2$) and the elastic coefficients ($k_1$, $k_2$) of the seismic mass and of the capsule body are such that the frequency of the relative movement (U) of the seismic mass relative to the housing has a first maximum between 0.5 and 10 Hz and a second maximum between 15 and 40 Hz.

13. The capsule of claim 12, wherein the first maximum is at 1.2 Hz.

14. The capsule of claim 12, wherein the second maximum is at 18 Hz.

15. The capsule of claim 12, wherein the elastic coefficients ($k_1$, $k_2$) of the restoring forces of the seismic mass and of the housing are in a ratio equal to 1.

16. The capsule of claim 11, wherein the seismic mass and the elastically deformable element are located so that the oscillating movement of the seismic mass and the deformation movement of the elastically deformable element are coaxial and are perpendicular to the wall of the patient's organ.

17. The capsule of claim 11, wherein the seismic mass and the elastically deformable element are located so that the oscillating movement of the seismic mass and the deformation movement of the elastically deformable element are transversely oriented and are parallel to the wall of the patient's organ.

18. The capsule of claim 11, comprising an elastically deformable element providing for oscillation of the seismic mass, wherein the elastically deformable element comprises at least one of: a cantilever beam, an engraved spring, and a spiral spring.

19. The capsule of claim 11, wherein the elastically deformable base comprises at least one of: a coil spring and a cantilever beam.

20. A method for harvesting energy in an intracorporeal medical capsule for a heart, comprising:
   anchoring an elastically deformable element to a wall of tissue within the heart, wherein the elastically deformable element extends from an exterior surface of the capsule;
   receiving mechanical energy via movement of the wall, a seismic mass elastically coupled inside the capsule to an energy harvesting element;
   receiving mechanical energy via movement of blood in the heart using the elastically deformable element; and
   utilizing, by the energy harvesting element, the mechanical energy received via the movement of the wall and the mechanical energy received via the movement of blood in the heart.

* * * * *